(12) United States Patent
Brooks-MacDonald (10) Patent No.: US 12,053,583 B2
(45) Date of Patent: Aug. 6, 2024

(54) REUSABLE LINER FOR USE WITH RESPIRATORY MASK AND METHOD OF MAKING SAME

(71) Applicant: Connie Brooks-MacDonald, Corbeil (CA)

(72) Inventor: Connie Brooks-MacDonald, Corbeil (CA)

(73) Assignee: Connie Brooks-MacDonald, Corbeil (CA)

( * ) Notice: Subject to any disclaimer, the term of this patent is extended or adjusted under 35 U.S.C. 154(b) by 357 days.

(21) Appl. No.: 17/209,694

(22) Filed: Mar. 23, 2021

(65) Prior Publication Data

US 2021/0299386 A1 Sep. 30, 2021

Related U.S. Application Data

(60) Provisional application No. 62/994,157, filed on Mar. 24, 2020.

(51) Int. Cl.
*A61M 16/06* (2006.01)

(52) U.S. Cl.
CPC . *A61M 16/0616* (2014.02); *A61M 2205/6081* (2013.01); *A61M 2207/00* (2013.01)

(58) Field of Classification Search
CPC ........... A61M 16/06–0694; A61M 2016/0661; A61M 2205/6081; A61M 2207/00; A62B 18/02; A62B 18/025; A62B 18/08; A42B 1/012
See application file for complete search history.

(56) References Cited

U.S. PATENT DOCUMENTS

| | | | |
|---|---|---|---|
| 8,997,742 B2 * | 4/2015 | Moore | A61M 16/06 128/200.24 |
| 2006/0048271 A1 * | 3/2006 | Totani | A42B 1/22 2/171.1 |
| 2006/0081251 A1 * | 4/2006 | Hernandez | A61M 16/06 128/206.24 |
| 2013/0220327 A1 * | 8/2013 | Barlow | A61M 16/0605 128/205.25 |
| 2014/0251334 A1 * | 9/2014 | Kramer | A61M 16/0875 128/205.25 |
| 2016/0213872 A1 * | 7/2016 | Paulk | A61M 16/0875 |
| 2018/0214655 A1 * | 8/2018 | Kooij | A61M 16/0611 |

* cited by examiner

*Primary Examiner* — Valerie L Woodward
(74) *Attorney, Agent, or Firm* — Reed Smith LLP; Hallie H. Wimberly (57) ABSTRACT

A reusable liner for use with a respiratory mask and a method of making same. The reusable liner has a body with an opening and an outer edge. A band of stretchable, elastic knit ribbing is fixed to the outer edge. The reusable liner is positionable over the respiratory mask and held in place by the band of elastic knit ribbing. The reusable liner is washable and reusable.

10 Claims, 8 Drawing Sheets

REUSABLE LINER FOR USE WITH RESPIRATORY MASK AND METHOD OF MAKING SAME

RELATED APPLICATION

This application claims priority to U.S. Provisional Application No. 62/994,157, filed Mar. 24, 2020, entitled, "REUSABLE LINER FOR USE WITH RESPIRATORY MASK", which is incorporated by reference in its entirety herein.

FIELD OF THE INVENTION

This invention relates to a reusable liner for use with a respiratory mask and method of making same. In particular, the current invention is directed to a reusable liner which is attachable to a respiratory mask such as a continuous positive airway pressure mask ("CPAP mask"), an automatic positive airway pressure mask ("APAP mask"), and a bilevel positive airway pressure mask ("BiPAP mask"), and a method of making same.

BACKGROUND OF THE INVENTION

Sleep apnea is a serious and potentially life threatening medical condition in which a person's airway becomes blocked many times during sleep, restricting oxygen intake and causing the person to wake up gasping for breath. It can affect anyone at any age, even children.

The most common type of sleep apnea is obstructive sleep apnea, which occurs when the upper airway gets blocked during sleep. Often, the blockage happens when the soft tissue in the back of the throat collapses and closes. Central sleep apnea occurs when the brain does not send proper signals to the muscles that control breathing. Mixed sleep apnea is a combination of the two and more rare.

Symptoms include loud snoring, disrupted sleep, morning headaches, poor concentration or memory loss, falling asleep while driving and excessive daytime sleepiness. Possible side effects from this condition include extreme fatigue, high blood pressure, strokes, heart attacks, motor vehicle collisions, work-related injuries and even death.

The most common treatment for sleep apnea is the use of a continuous positive airway pressure ("CPAP") machine. The CPAP machine consists of three main parts. First, a mask fits over the nose and/or mouth of a user's face, with some masks fitting under the nose. The mask is held in place with straps while sleeping. Second, there is a motor in a separate machine that blows air. Third, a long, cylindrical hollow plastic tube connects the CPAP machine to the CPAP mask. Air is compressed in the CPAP machine and then delivered through the hose to the mask. The continuous pressure of blowing air travels through the throat keeping the airways open while sleeping.

There are three types of positive airway pressure machines, as described herein.

CPAP machines are only set to a single pressure that remains consistent during its use.

Automatic Positive Airway Pressure ("APAP") machines rely on the same principles as CPAP except the pressure settings are not limited to a single pressure, but to a range of pressures. The APAP machine adjusts to the ideal pressure with each breath.

Bilevel Positive Airway Pressure (BiPAP) machines have two pressure settings: the prescribed pressure for inhalation ("ipap"); and a lower pressure for exhalation ("epap"). The "bilevel" refers to the two air pressure levels that the machine is able to alternate between. This allows a user to get more air in and out of their lungs. Individuals who use CPAP, APAP, or BiPAP machines are diagnosed with sleep apnea by a doctor following an overnight sleep study.

Most respiratory masks, such as those used with CPAP, APAP, or BiPAP machines, are typically made of silicone, rubber, vinyl, or a nylon based product. The materials from which these masks are made from can cause skin sensitivity for some users by causing sweating and blocking pores. Other users may have allergies to the materials from which the masks are made, such as silicone, or they may have dry sensitive skin that is irritated by the mask. Use of face cream is generally not recommended since the mask contacts the skin directly while sleeping. Also, the masks can become dirty collecting dust, skin cells, bacteria, oil, and more over time. Older CPAP cushions break down over time and can become abrasive and uncomfortable to user. Often, the straps, which hold the mask against a user's face, are tightened strongly to stop air leakage which increases the amount of pressure on the chin, cheeks, nose and back of the head of a user causing pressure marks and additional discomfort and pain. It is reported that as many as 50 percent of people stop using CPAP therapy due to discomfort from the equipment.

SUMMARY OF THE INVENTION

The applicant has appreciated that there is a need for a reusable liner for use with a respiratory mask that fits snugly and securely around a mask and does not bunch up, become misaligned, or slip off of the mask and become uncomfortable for a user. Accordingly, the applicant has invented a reusable liner for use with a respiratory mask which has advantages over current liners.

In particular, the current invention is directed to a reusable liner for use with a respiratory mask that:
1. Can be reused many times and is washable;
2. Is manufactured from stretchy absorbent fabrics, such as cotton, hemp, and bamboo, which fabrics offer softness, durability, absorbency, and antibacterial qualities;
3. Lessens textile landfill waste and is more environmentally friendly, for example since the plants from which the cotton, hemp, and bamboo fabrics are derived are sustainable plants that do not require the use of pesticides, herbicides or other chemical fertilizers to grow;
4. Has a band of stretchable, elastic knit ribbing for a more uniform and sturdy fit around the mask with less bulk allowing the head band and/or cheek strap gear to connect to the mask easily; and
5. The reusable liners fit carefully over the soft cushion of the mask and are held securely in place by the elastic knit ribbing causing less movement of fabric on the face so that the liner will not fall off the mask.

In one embodiment, the invention resides in a reusable liner for use with a respiratory mask, the liner having: a body with at least one inner opening and an outer edge, the outer edge being attached to a band of elastic ribbing, such that the reusable liner is positionable on the respiratory mask and is held in place by the band of elastic ribbing.

Preferably, the band of elastic ribbing comprises a generally rectangular strip of ribbing material which has been folded in half along a lengthwise centre line of the strip of ribbing material and longitudinal edges thereof are sewn and/or serged to the outer edge of the body.

Preferably, the at least one opening is a shape selected from the group consisting of: oval, triangular, round, and elliptical.

Preferably, the at least one opening comprises a first opening and a second opening, the first opening is proximate the middle of the body and the second opening is located above the first opening.

Preferably, the body is made from a material selected from the group consisting of: cotton, hemp, bamboo, polyester, and organic fabrics mixed with spandex.

Still preferably, the respiratory mask is used with a device selected from the group consisting of: a continuous positive airway pressure device, an automatic positive airway pressure device, and a bilevel positive airway pressure device.

Preferably, a dot is fixed on top of the ribbing to better assist the user in positioning the liner on the mask correctly with the dot positioned at the top of the respiratory mask.

More preferably, the dot is a selected colour signifying a specific size and/or type of reusable liner.

Preferably, the liner is used with a mask selected from the group consisting of a respiratory mask, full face mask, a minimal-contact full face mask, and a nasal respiratory mask.

In another embodiment, the invention resides in a method of making a reusable liner for use with a respiratory mask, comprising the steps of: forming a main body from material with at least one opening in the main body; forming a band of ribbing from a generally rectangular strip of ribbing material which is folded in half along a lengthwise centre line; and attaching the band to the body.

Preferably, the band of ribbing is attached to the body by sewing and/or serging.

Further and other features of the invention will be apparent to those skilled in the art from the following detailed description of the embodiments thereof.

BRIEF DESCRIPTION OF THE DRAWINGS

Reference may now be had to the following detailed description taken together with the accompanying drawings in which.

DETAILED DESCRIPTION OF THE PREFERRED EMBODIMENTS

Figure 1:
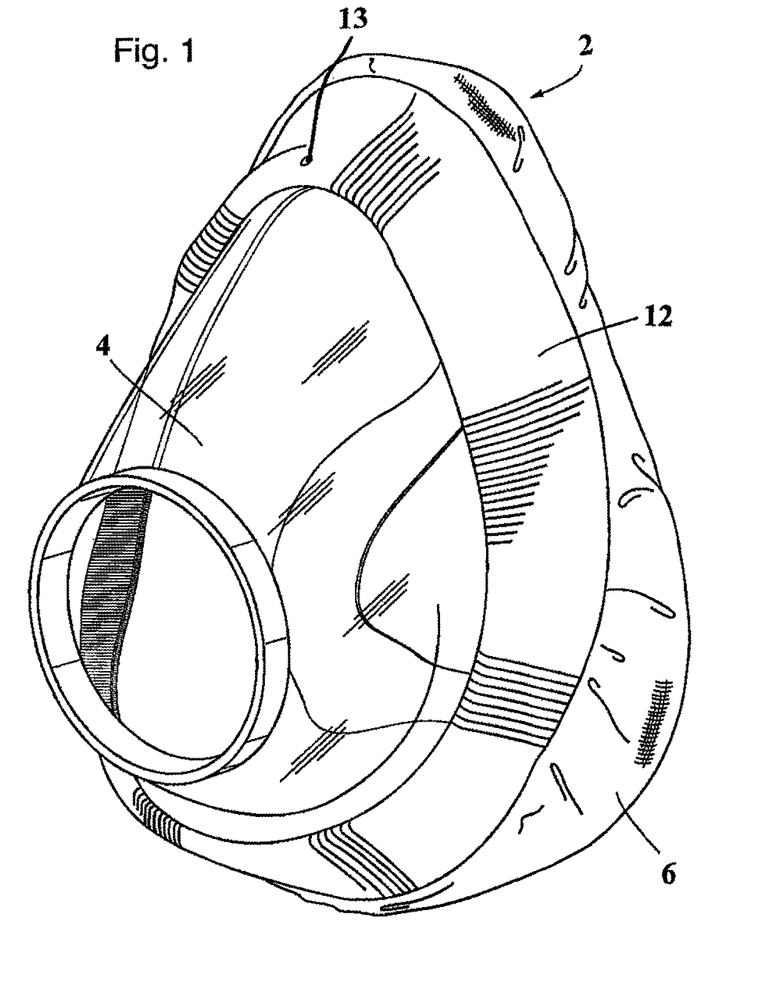
FIG. 1 shows a full face reusable liner for use with a full face respiratory mask positioned on a full face respiratory mask in accordance with one embodiment of the current invention.

FIG. 1 shows a reusable full face liner 2. Preferably, the reusable full face liner 2 is used with a respiratory mask 4. The mask 4 shown in FIG. 1 is a Continuous Positive Airway Pressure Machine ("CPAP") mask. The reusable full face liner 2 could also be used with masks for other respiratory machines including but not limited Automatic Positive Airway Pressure (APAP) machines and Bilevel Positive Airway Pressure (BiPAP) machines.

Figure 2:
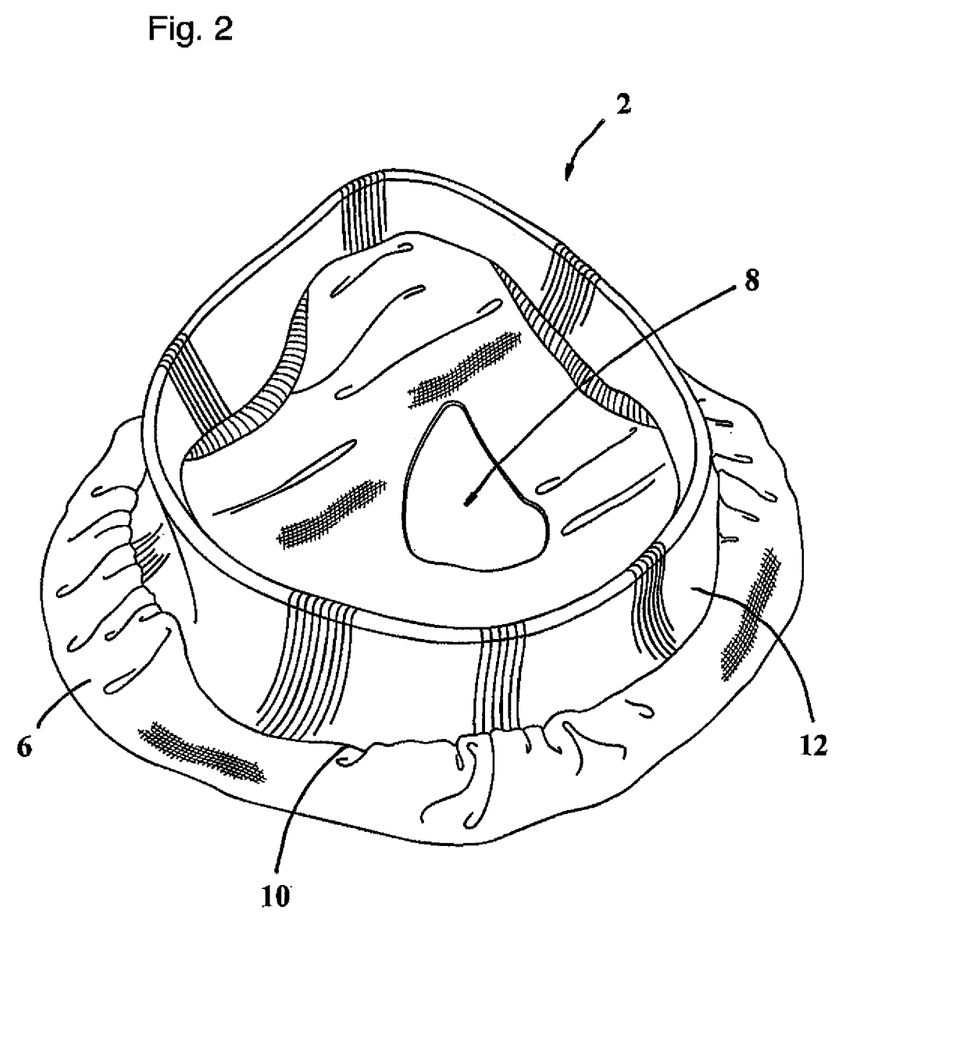
FIG. 2 shows the full face reusable liner for use with the full face respiratory mask of FIG. 1 in perspective bottom view.

As shown in FIG. 2, the reusable full face liner 2 has a main body 6. The main body 6 has an inner opening 8 and an outer edge 10. Preferably, the main body 6 has a height of approximately 6¼ inches and a width of approximately 5¾ inches. The inner opening may be generally oval shaped, triangular shaped, round shaped, elliptical shaped, or another shape appropriate for use with a respiratory mask, and is not limited to the shape shown in the Figures or described herein. Preferably, the generally triangular shaped opening 8 shown in FIG. 2 has a height of approximately 2½ inches and a base of approximately 1½ inches.

A stretchable, elastic knit band of ribbing 12 is affixed to the outer edge 10. Preferably, the ribbing 12 is made from a generally rectangular strip of ribbing material which is folded in half along a lengthwise centre line and the longitudinal edges of the ribbing 12 are sewn and/or serged to the outer edge 10 of the main body 6. Preferably, the ribbing 12 as shown on the reusable full face liner 2 in FIG. 2 is formed from a strip of ribbing material that is generally rectangular and has a length of approximately 9½ inches and a height of approximately 2 inches. The generally rectangular strip is then folded in half along a lengthwise centre line to create a folded strip having a height or approximately 1 inch. The ends of the folded generally rectangular strip are then sewn together so that the folded generally rectangular strip is formed into a circular ring. Alternatively, the approximately 2 inch ends of the generally rectangular strip can be sewn together to form a circular strip which is then folded along a lengthwise centerline to create the folded circular ring. This folded circular ring forms the band of ribbing 12 which is then affixed to the outer edge 10, preferably by sewing and/or serging. Ribbing material is a special type of knit fabric that has longitudinal lines across the fabric which form bumps or ribs. Ribbing is able to stretch without losing its shape and is frequently used to make cuffs on a sweater, necklines on shirts, and with socks.

In a preferred embodiment, a dot 13, as shown in FIG. 1, is fixed, for example embroidered or sewn, on top of the ribbing 12 to better assist the user in positioning the liner on the mask correctly, with the dot 13 positioned at the top of the reusable full face liner 2. Further, the dot 13 can be different colours signifying different sizes and/or types of reusable liners.

In a preferred embodiment, the main body 6 of the reusable full face liner 2 is made from an absorbent, stretchable material such as cotton, hemp, bamboo, polyester, or organic fabrics mixed with some spandex. In one preferred embodiment, the fabric is 95% organic cotton, organic hemp, or organic bamboo, mixed with 5% spandex. Organic cotton, organic hemp or organic bamboo are preferred since these organic materials are processed into fibre using organic chemicals that are covered under the Oeko-Tex Standard 100 certification and are 100% recyclable.

Figure 3:
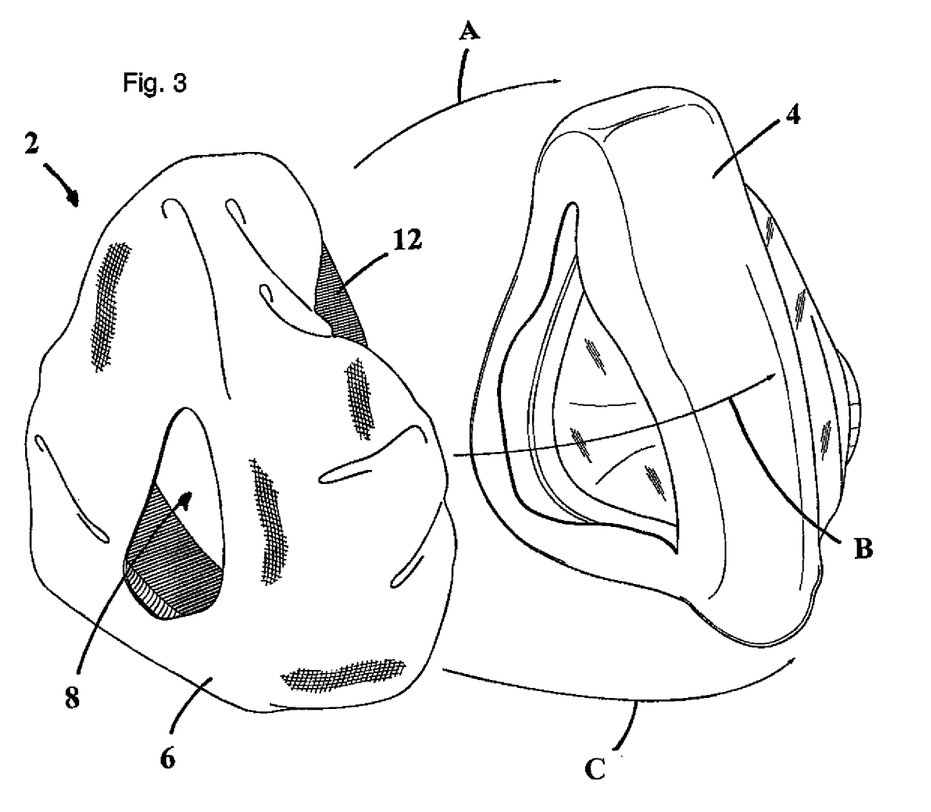
FIG. 3 shows the full face reusable liner for use with the full face respiratory mask of FIG. 1 being positioned on the full face respiratory mask.

As shown in FIG. 3, the reusable full face liner 2 is positioned on the full face mask 4 by stretching the band of ribbing 12 and positioning the band of ribbing 12 over the outer edges of the full face mask 4 in direction of arrows A, B, and C. Once the reusable full face liner 2 has been positioned on the full face mask 4, it is held in place by the ribbing 12. Because of the properties of the ribbing 12, the full face liner 2 fits over the mask 4 more securely and better resists falling off, becoming misaligned, or bulking or bunching up.

Figure 4:
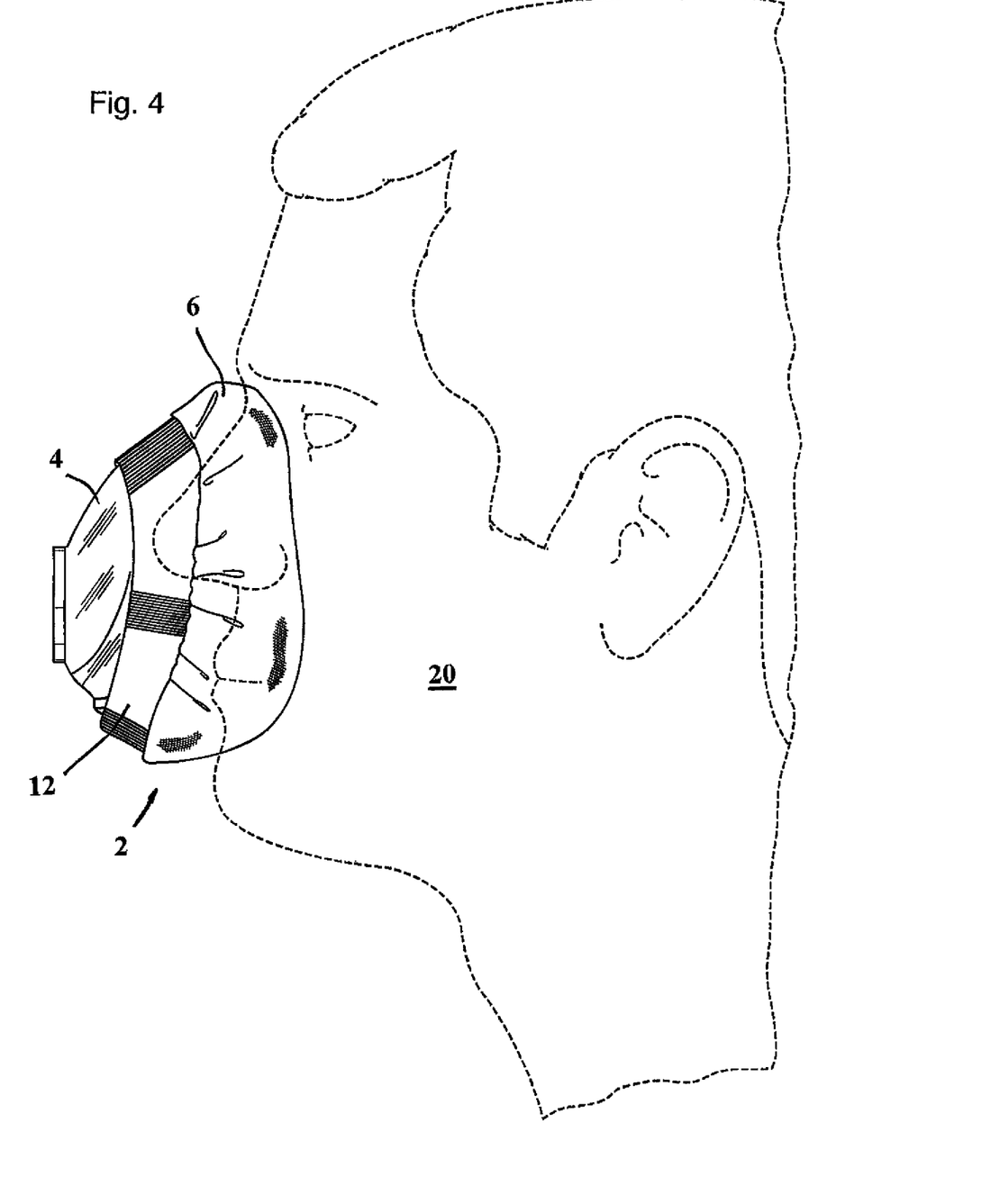
FIG. 4 shows the full face reusable liner for use with the full face respiratory mask of FIG. 1 positioned on the full face respiratory mask in use.

FIG. 4 shows the reusable full face liner 2 positioned on the mask 4 in use on a user's face 20. As shown, the body 6 of the full face liner 2 is in contact with the user's face with the user's nose positioned through the inner opening 8, shown in FIGS. 2 and 3. The inner opening 8 permits air flow from an air source (not shown) to be received by the user through the inner opening 8.

Figure 5:
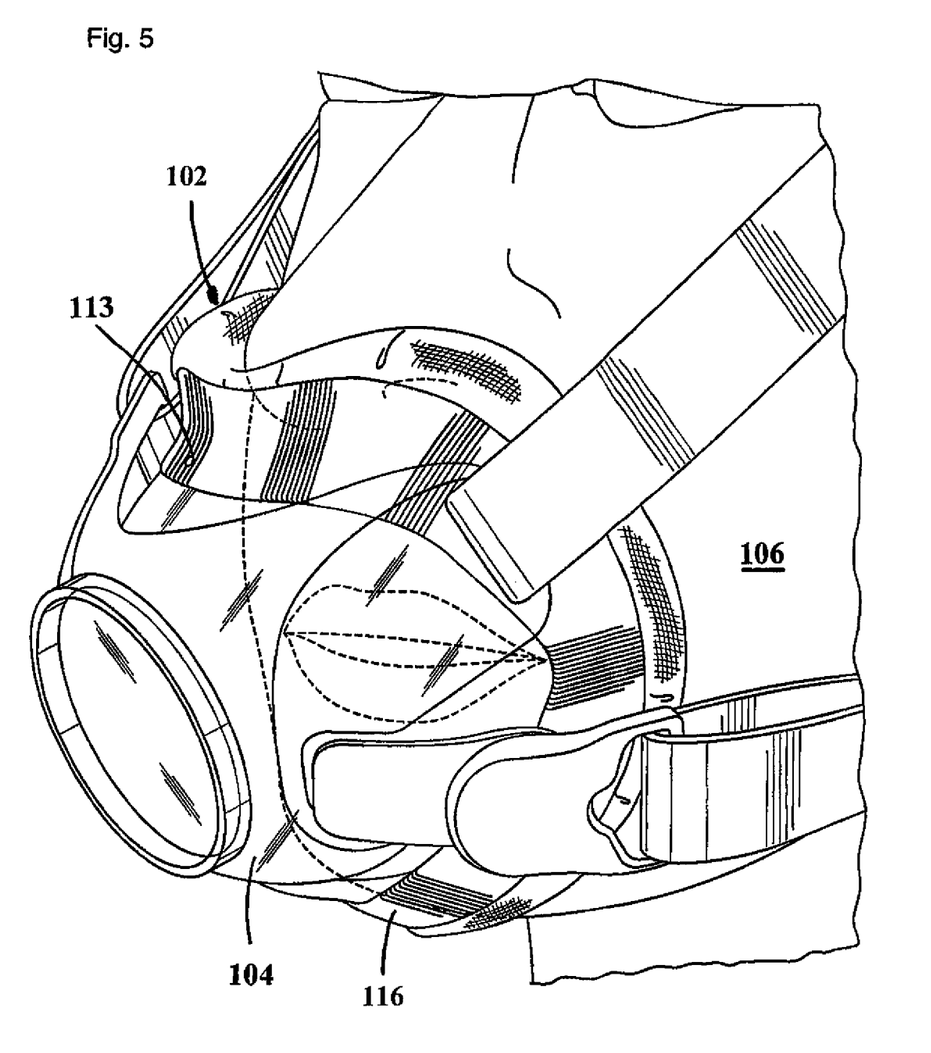
FIG. 5 shows a minimal-contact full face reusable liner for use with a minimal-contact full face respiratory mask in accordance with another embodiment of the invention, with the minimal-contact full face reusable liner positioned on the minimal-contact full face respiratory mask and in use.

FIG. 5 shows a reusable minimal-contact full face liner 102 for use with a minimal-contact full face respiratory mask 104 in accordance with another embodiment of the invention. The reusable minimal-contact full face liner 102 is positioned on the minimal-contact full face respiratory mask 104 and is positioned on a user's face 106.

Figure 6:
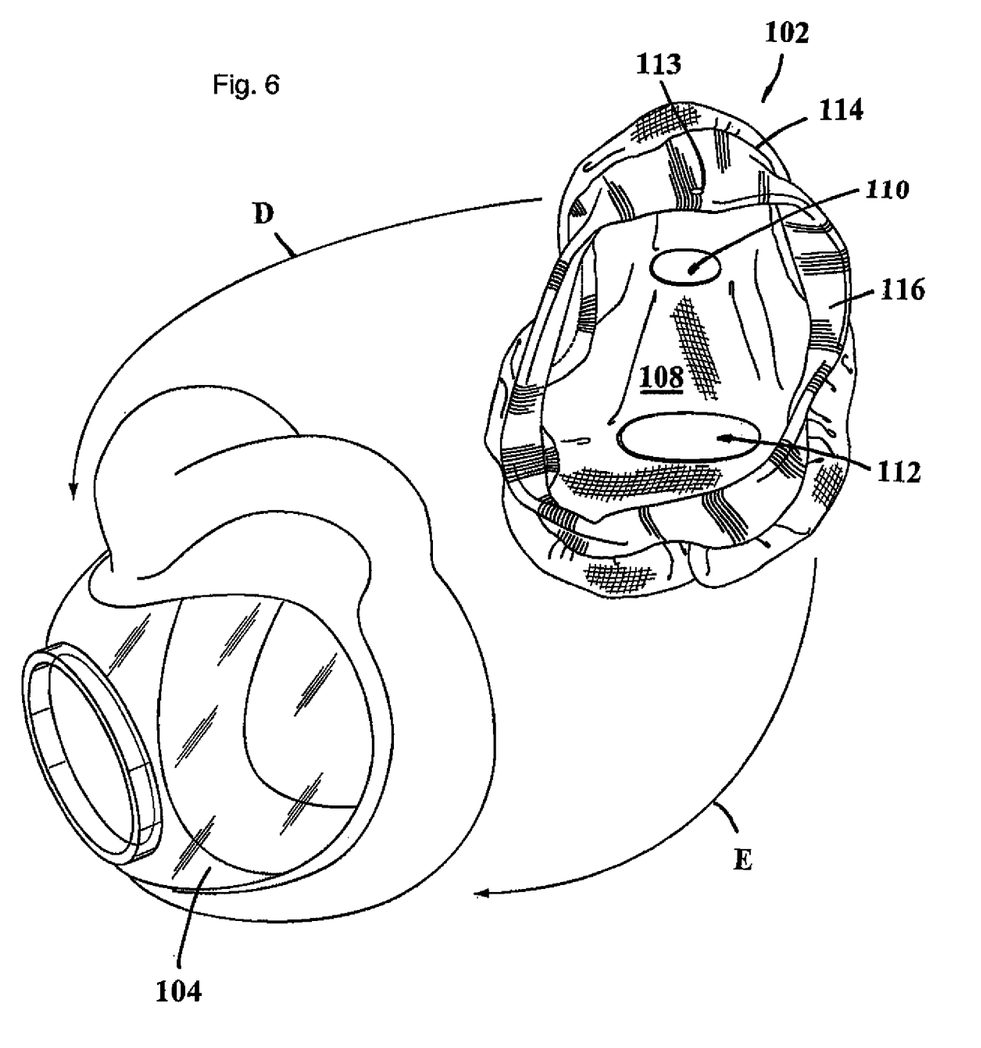
FIG. 6 shows the reusable liner for use with the minimal-contact full face respiratory mask of FIG. 5 being positioned on the minimal-contact full face respiratory mask.

As shown in FIG. 6, the reusable minimal-contact full face liner 102 has a main body 108 with a first opening 110 and a second opening 112, positioned below the first opening 110. The first opening 110 is designed so that a user's nose can sit on top of the first opening 110 when the reusable minimal-contact full face liner 102 is in use and thereby in fluid communication with a respiratory machine (not shown). The second opening 112 is larger than the first opening 110 and is designed so that a users' mouth is able to be in communication with the minimal-contact full face respiratory mask 102 and thereby in fluid communication with a respiratory machine (not shown) when connected to the minimal-contact full face respiratory mask 102. Preferably the first opening 110 is generally oval shaped, having a height of approximately ½ inch and a width of approximately 1¾ inches. Preferably, the second opening 112 is generally oval shaped, having a height of approximately 1 inch, and a width of approximately 2 inches. While the first opening 110 and the second opening 112 are shown as being generally oval shaped, it could be triangular shaped, round shaped, elliptical shaped, or another shape appropriate for use with a respiratory mask, and are not limited to the shape shown in FIG. 6 or described herein.

The body 108 of the reusable minimal-contact full face liner 102 has an outer edge 114 with a stretchable, elastic knit band of ribbing 116 affixed to the outer edge 114. Preferably, the ribbing 116 is made from a generally rectangular strip of ribbing material which is folded in half along a lengthwise centre line and the longitudinal edges of the ribbing 116 are sewn and/or serged to the outer edge 114 of the main body 108. Preferably, the ribbing 116 as shown on the liner 102 in FIG. 6 is formed from a strip of ribbing material that is generally rectangular and has a length of approximately 9½ inches and a height of approximately 2 inches. The generally rectangular strip is then folded in half along a lengthwise centre line to create a folded strip having a height or approximately 1 inch. The ends of the folded generally rectangular strip are then sewn so that the folded generally rectangular strip is sewn into a circular ring. Alternatively, the approximately 2 inch ends of the generally rectangular strip can be sewn together to form a circular strip which is then folded along a lengthwise centerline to create the folded circular ring. This circular ring forms the band of ribbing 116 which is then affixed to the outer edge 114, preferably by sewing and/or serging.

In a preferred embodiment, the main body 108 of the reusable minimal-contact full face liner 102 is made from an absorbent, stretchable material such as cotton, hemp, bamboo, polyester, or organic fabrics, mixed with some spandex, as previously described.

As shown in FIG. 6, the reusable minimal-contact full face liner 102 is positioned on the minimal-contact full face respiratory mask 104 by stretching the band of ribbing 116 and positioning the band of ribbing 116 over the outer edges of the mask 104 in direction of arrows D and E. Once the reusable minimal-contact full face liner 102 has been positioned on the minimal-contact full face respiratory mask 104, it is held in place by the ribbing 116. Because of the properties of the ribbing 116, the reusable minimal-contact full face liner 102 fits over the mask 104 more securely and better resists falling off, becoming misaligned, or bulking or bunching up.

In a preferred embodiment, a dot 113, as shown in FIGS. 5 and 6, is fixed, for example embroidered or sewn, on top of the ribbing 116 to better assist the user in positioning the liner on the mask correctly, with the dot 113 positioned at the top of the reusable minimal-contact face liner 102. Further, the dot 113 can be different colours signifying different sizes and/or types of reusable liners.

Figure 7:
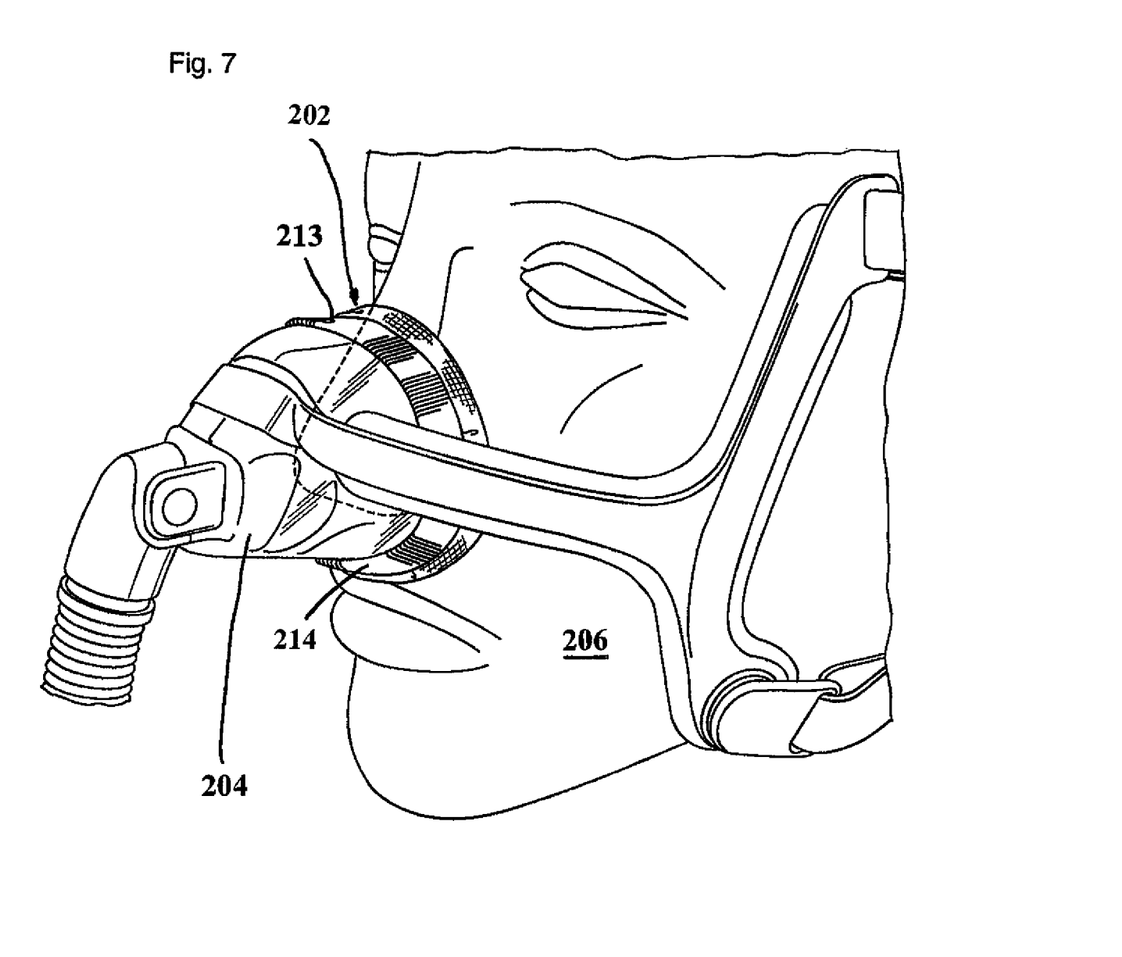
FIG. 7 shows a reusable nasal liner for use with a nasal respiratory mask in accordance with another embodiment of the invention, with the reusable nasal liner positioned on the nasal mask and in use.

FIG. 7 shows a reusable nasal liner 202 for use with a nasal respiratory mask 204 in accordance with another embodiment of the invention. As shown, the reusable nasal liner 202 is positioned on the nasal respiratory mask 204 which is positioned over a nose on a user's face 206.

Figure 8:
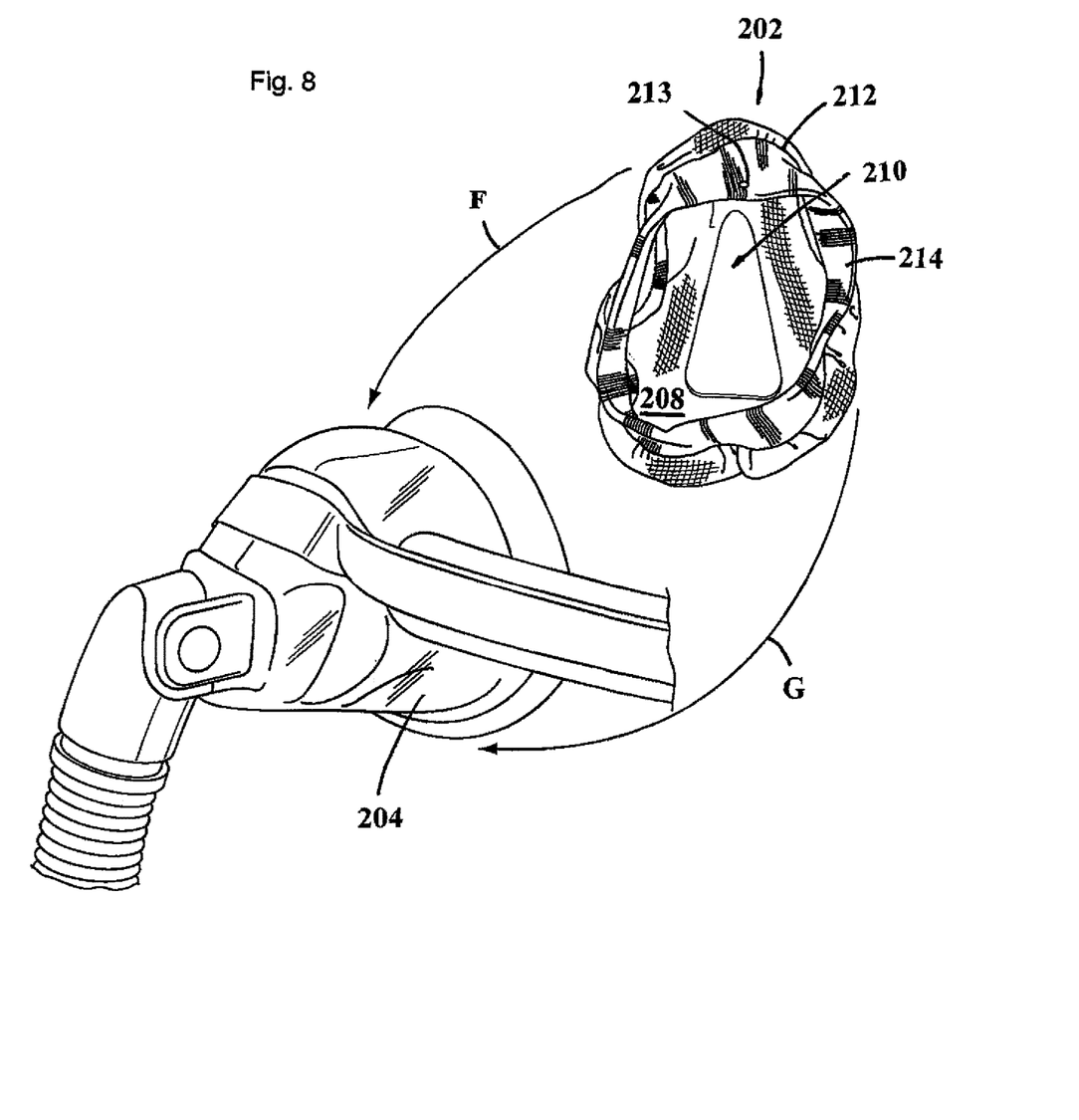
FIG. 8 shows the reusable nasal liner of FIG. 7 being positioned on the nasal respiratory mask.

FIG. 8 shows the reusable nasal liner 202 of FIG. 7 being positioned on the respiratory nasal mask 204. As shown, the reusable nasal liner 202 has a main body 208 with an opening 210. Preferably, the main body 208 has a height of approximately 4¾ inches and a width of approximately 4 inches. The opening 210 is sized and shaped so that a user's nose can fit through the opening 210 when the reusable nasal liner 202 is in use. Thus, the user's nose fits through the opening 210 and is in communication with the nasal respiratory mask 202 and thereby in fluid communication with a respiratory machine (not shown) when connected to the nasal respiratory mask 202. The opening 210 may be generally oval shaped, triangular shaped, round shaped, elliptical shaped, or another shape appropriate for use with a respiratory mask, and is not limited to the shape shown in the Figures or described herein. Preferably, the opening 210 is generally triangular and has a height of approximately 1¾ inches and a base of approximately 1 inch.

The main body 208 of the reusable nasal liner 202 has an outer edge 212 with a band of ribbing 214 is affixed to the outer edge 212. Preferably, the ribbing 214 is made from a generally rectangular strip of ribbing material which is folded in half along a lengthwise centre line and the longitudinal edges of the ribbing 214 are sewn and/or serged to the outer edge 212 of the main body 208. Preferably, the ribbing 214 of the liner 202 shown in FIG. 8 is formed from a strip of ribbing that is generally rectangular and has a length of approximately 5½ inches and a height of approximately 2 inches. The generally rectangular strip is then folded in half along a lengthwise centerline to create a folded strip having a height of approximately 1 inch. The ends of the folded generally rectangular strip are then sewn so that the folded generally rectangular strip is sewn into a circular ring. Alternatively, the approximately 2 inch ends of the generally rectangular strip can be sewn together to form a circular strip which is then folded along a lengthwise centerline to create the folded circular ring. This circular ring forms the band of ribbing 214 which is then affixed to the outer edge 212, preferably by sewing and/or serging.

In a preferred embodiment, a dot 213, as shown in FIGS. 7 and 8, is fixed, for example embroidered or sewn, on top of the ribbing 214 to better assist the user in positioning the liner on the mask correctly, with the dot 213 positioned at the top of the reusable nasal liner 202. Further, the dot 213 can be different colours signifying different sizes and/or types of reusable liners.

In a preferred embodiment, the main body 208 of the reusable nasal liner 202 is made from an absorbent, stretchable material such as cotton, hemp, bamboo, polyester, or organic fabrics, mixed with some spandex, as previously described.

As shown in FIG. 8, the reusable nasal liner 202 is positioned on the nasal respiratory mask 204 by stretching the band of ribbing 214 and positioning the band of ribbing 214 over the outer edges of the mask 204 in direction of arrows F and G. Once the reusable liner 202 has been positioned on the mask 204, it is held in place by the ribbing 214. Because of the properties of the ribbing 214, the reusable nasal liner 202 fits over the nasal respiratory mask 204 more securely and better resists falling off, becoming misaligned, or bulking or bunching up.

It is appreciated that the reusable liners described herein can be made in various sizes to be used with corresponding masks of different sizes.

Although this disclosure has described and illustrated certain preferred embodiments of the invention, it is also to be understood that the invention is not restricted to these particular embodiments rather, the invention includes all embodiments which are functional, or mechanical equivalents of the specific embodiments and features that have been described and illustrated herein.

It will be understood that, although various features of the invention have been described with respect to one or another of the embodiments of the invention, the various features and embodiments of the invention may be combined or used in conjunction with other features and embodiments of the invention as described and illustrated herein.

What is claimed is:

1. A reusable liner for use with a respiratory mask, the liner having: a body with at least one inner opening and an outer edge, the outer edge being attached to a band of elastic ribbing, such that the reusable liner is positionable on the respiratory mask and is held in place by the band of elastic ribbing, wherein the band of elastic ribbing comprises a stretchable knit band of ribbing, and wherein a dot is fixed on top of the band of elastic ribbing to better assist a user in positioning the liner on the respiratory mask correctly with the dot positioned at the top of the respiratory mask.

2. The reusable liner for use with a respiratory mask of claim 1, wherein the band of elastic ribbing comprises a generally rectangular strip of ribbing material which has been folded in half along a lengthwise centre line of the strip of ribbing material and longitudinal edges thereof are sewn and/or serged to the outer edge of the body.

3. The reusable liner for use with a respiratory mask of claim 1, wherein the at least one opening is a shape selected from the group consisting of: oval, triangular, round, and elliptical.

4. The reusable liner for use with a respiratory mask of claim 1, wherein the at least one opening comprises a first opening and a second opening, first opening is proximate the middle of the body and the second opening is located above the first opening.

5. The reusable liner for use with a respiratory mask of claim 1, wherein the body is made from a material selected from the group consisting of: cotton, hemp, bamboo, polyester, and organic fabrics mixed with spandex.

6. The reusable liner for use with a respiratory mask of claim 1, wherein the respiratory mask is used with a device selected from the group consisting of: a continuous positive airway pressure device, an automatic positive airway pressure device, and a bilevel positive airway pressure device.

7. The reusable liner for use with a respiratory mask of claim 1, wherein the dot is a selected colour signifying a specific size and/or type of reusable liner.

8. The reusable liner for use with a respiratory mask of claim 1, wherein the liner is used with a mask selected from the group consisting of a respiratory mask, full face mask, a minimal-contact full face mask, and a nasal respiratory mask.

9. A method of making a reusable liner for use with a respiratory mask, comprising the steps of:
   A. Forming a main body from material with at least one opening in the main body;
   B. Forming a band of ribbing from a generally rectangular strip of ribbing material which is folded in half along a lengthwise centre line, wherein the band of ribbing comprises a stretchable, elastic knit band of ribbing;
   C. Attaching the band to the body; and
   D. Fixing a dot on top of the band of ribbing to better assist a user in positioning the liner on the respiratory mask correctly with the dot positioned at the top of the respiratory mask.

10. The method of making a reusable liner for use with a respiratory mask of claim 9, wherein the band of ribbing is attached to the body by sewing and/or serging.

\* \* \* \* \*